(12) United States Patent
Nørgaard et al.

(10) Patent No.: US 8,435,394 B2
(45) Date of Patent: May 7, 2013

(54) ELECTRONIC DEVICE ASSEMBLY WITH SAFETY ELECTRIC CONNECTOR

(75) Inventors: Jesper Bach Nørgaard, Virum (DK); Lars Aagaard, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 700 days.

(21) Appl. No.: 12/532,950

(22) PCT Filed: Mar. 14, 2008

(86) PCT No.: PCT/EP2008/053107
§ 371 (c)(1),
(2), (4) Date: Jan. 26, 2010

(87) PCT Pub. No.: WO2008/119648
PCT Pub. Date: Oct. 9, 2008

(65) Prior Publication Data
US 2010/0133099 A1 Jun. 3, 2010

Related U.S. Application Data

(60) Provisional application No. 60/921,560, filed on Apr. 3, 2007.

(30) Foreign Application Priority Data

Mar. 30, 2007 (EP) .................................. 07105356

(51) Int. Cl.
*H01R 13/447* (2006.01)
*G01N 27/416* (2006.01)
(52) U.S. Cl.
USPC .............. 204/406; 422/117; 439/53; 439/149

(58) Field of Classification Search .......... 204/400–407; 422/68.1, 117; 435/4–40.52; 439/43–85, 439/92–108, 133–150, 188, 620.01–620.34, 439/892–893
See application file for complete search history.

(56) References Cited

U.S. PATENT DOCUMENTS 5,141,868 A 8/1992 Shanks et al.
5,286,362 A 2/1994 Hoenes et al.
(Continued)

FOREIGN PATENT DOCUMENTS

EP 753906 1/1997
EP 1494124 1/2005
(Continued)

OTHER PUBLICATIONS

Machine Translation of EP 753906.

*Primary Examiner* — J. Christopher Ball
(74) *Attorney, Agent, or Firm* — Wesley A. Nicolas; Marc A. Began; Reza Green

(57) ABSTRACT

The application provides an assembly comprising a housing (20) having an electrical housing connector (50) and a strip port (40) for a BGM sensor arranged in the vicinity of the electrical connector. The assembly further comprises an external electrical connector (60) adapted for releasable connection to the housing connector, wherein the external electrical connector comprises a portion (62) adapted to block the port opening when the external electrical connector is connected to the housing connector, thereby preventing insertion of a strip in the port when the two connectors are connected to each other. In this way it is prevented in a simple and cost-effective manner that a patient via an inserted strip is subjected to a too high voltage or current supplied to the circuitry of the electronic device.

12 Claims, 3 Drawing Sheets

U.S. PATENT DOCUMENTS

| | | |
|---|---|---|
| 5,288,636 A | 2/1994 | Pollmann et al. |
| 5,437,999 A | 8/1995 | Diebold et al. |
| 5,597,532 A | 1/1997 | Connolly |
| 6,873,268 B2 | 3/2005 | Lebel et al. |
| 6,936,029 B2 | 8/2005 | Mann et al. |
| 7,303,549 B2 | 12/2007 | Flaherty et al. |
| 8,025,509 B2 * | 9/2011 | Bernstein et al. ............. 439/135 |
| 2002/0060247 A1 | 5/2002 | Krishnaswamy et al. |
| 2003/0065308 A1 | 4/2003 | Lebel et al. |
| 2004/0167464 A1 | 8/2004 | Ireland et al. |
| 2006/0261871 A1 | 11/2006 | Becker et al. |

FOREIGN PATENT DOCUMENTS

| | | |
|---|---|---|
| WO | WO 2006/077263 | 7/2006 |
| WO | WO 2007/000427 | 1/2007 |

* cited by examiner

ELECTRONIC DEVICE ASSEMBLY WITH SAFETY ELECTRIC CONNECTOR

CROSS-REFERENCE TO RELATED APPLICATIONS

This application is a 35 U.S.C. §371 national stage application of International Patent Application PCT/EP2008/053107 (published as WO 2008/119648), filed Mar. 14, 2008, which claimed priority of European Patent Application 07105356.5, filed Mar. 30, 2007; this application further claims priority under 35 U.S.C. §119 of U.S. Provisional Application 60/921,560, filed Apr. 3, 2007.

The present invention generally relates to devices used for the testing of body fluids such as blood and urine and more specifically to portable patient-operated devices for the testing of body fluids.

BACKGROUND OF THE INVENTION

In the disclosure of the present invention reference is mostly made to the treatment of diabetes by injection or infusion of insulin, however, this is only an exemplary use of the present invention.

Those people who have "type 1 diabetes," also called insulin-dependent diabetes mellitus (IDDM), do not produce insulin and need regular injections or infusions of insulin to maintain their blood glucose at a normal level. As a result, people with type 1 diabetes must test their blood sugar regularly, often several times a day, to determine the amount of insulin to be injected or infused. Devices for testing glucose levels in blood are known in the art and may typically comprise a glucose sensor adapted to receive a test strip with a blood sample, the sensor being arranged inside a housing behind a strip port through which the strip can be inserted into the sensor, see e.g. U.S. Pat. No. 5,597,532, which is hereby incorporated by reference in its entirety. Many other electrochemical and colorimetric test devices are known in the art. In general such a device is termed a blood glucose meter or BGM for short.

A BGM will typically be a pocket-sized portable device adapted to be carried by the diabetic user and will thus be battery operated. The batteries (or more correctly: electric cell(s)) may be disposable or rechargeable. In the latter case the BGM normally has an electrical power inlet connector allowing the rechargeable batteries to be charged in the BGM, either by connecting the BGM to a charger via a cable or by placing it in a charging cradle, the charger or cradle being connected to a utility power outlet. Examples of charging arrangements for BGM devices are shown in e.g. US 2002/0060247, US 2004/016746, US 2006/0261781 and EP 1 494 124 which are hereby incorporated by reference.

If the BGM, for any purpose, can be connected to an external device by an electrical connection, special care must be taken to minimise the possible leakage current through to the BGM and ultimately the user. With a built in blood glucose strip port, the patient may be in galvanic contact with the medical device through the strip when the blood is applied and if the medical device simultaneously is connected to an external system (e.g. a PC for the exchange of data or a wall plug charger) the possible leakage current might be too high. To prevent this is possible to reduce the leakage current by galvanic isolation of the strip sensor unit from the rest of the system. Further, it may be possible to use special medical-grade chargers or other peripheral equipment which has been adapted to minimize the risk of supplying a high voltage or current to an absolute minimum.

Having regard to the above, it is the object of the present invention to provide a device for the testing of body fluids which can be connected electrically to an external device or system, which is safe in use and which can be manufactured in a cost-effective manner. It is a further object of the invention to provide such a device which is easy to use and operate and which protects against incorrect use.

DISCLOSURE OF EXEMPLARY EMBODIMENTS OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention, an electronic device assembly is provided, comprising a housing having an interior, electric circuitry arranged in the interior, and an electrical housing connector in communication with the exterior. The housing is provided with a port opening arranged in the vicinity of the electrical connector. An analyte sensor is arranged in the housing in communication with the port opening. The assembly further comprises an external electrical connector adapted for releasable connection to the housing connector, whereby in a situation of use an electrical contact can be established between the two connectors, wherein the external electrical connector comprises a portion adapted to block the port opening when the external electrical connector is connected to the housing connector, thereby physically preventing insertion of an object in the port opening when the two connectors are connected to each other.

In this way it is prevented in a simple and cost-effective way that a patient via an inserted strip is subjected to a too high voltage or current supplied to the circuitry of the electronic device. The too high voltage or current may be provided by using either a wrong type of peripheral equipment or defective peripheral equipment. Indeed, in such a case the primary protection for the patient is due to the basic construction of the device, e.g. using a housing of non-conductive materials. The connector may be adapted for data communication (one or two-way), for general power supply to the circuitry, for charging an internal battery or a combination of these. For example, a standard USB connector would enable charging from a wall plug or a PC USB port, as well as communication via a PC USB port.

The portion on the external electrical connector adapted to block the port opening when the external connector is connected to the housing connector may be a male extension on the connector adapted to be positioned in front of the port opening or it may be adapted to engage the port opening per se or it may be adapted to engage a recessed portion around the port opening. When the male extension is adapted to positively engage a corresponding female structure, this can be used to prevent incorrect connection of the connector (e.g. trying to connect the connector 180° upside-down) if the housing does not allow the male extension to be fully inserted.

In an exemplary embodiment the electronic device assembly comprises a rechargeable power source electrically connected to the housing connector. The electronic device assembly may further include a charging apparatus comprising an electric power source connector, an electric outlet in communication with the external electrical connector, and electric power circuitry connected to the power source connector and the electric outlet and adapted to change a characteristic of electric power supplied to the electric circuitry before being supplied the electric outlet. Such a charging apparatus is typically termed a "charger" or a "power adaptor". Typically the power circuitry is adapted to change the voltage. The circuitry may be in the form of a traditional step-down transformer or it may be of the electronically controlled type. The electric power source connector may be a utility power plug, e.g. a 100-240V wall plug or it may be a 6-24V car plug type. Typically the external electrical connector is connected to the electric outlet via a cable.

In a further exemplary embodiment of the electronic device assembly the sensor is a physiological analyte sensor, e.g. a glucose sensor adapted to receive a blood glucose test strip. The port opening and the analyte sensor may correspondingly be adapted to receive a strip-formed member carrying a specimen to be analyzed by the sensor.

The electronic device assembly may be provided with one or more additional features such as a display for displaying an analyte value, keys allowing a user to enter data and/or commands, a communication port for transmitting and/or receiving data, a wireless receiver for receiving data, a wireless transmitter for transmitting analyte data, a processor for calculating patient treatment suggestions based on analyte sensor data.

When the electronic device assembly is in the form of a BGM, it may be used as part of a diabetes management system comprising an insulin delivery device such as a pump adapted for subcutaneous infusion of an insulin containing drug. In such a system the BGM may be adapted to serve as the main user interface for the system, e.g. serving as a remote controller providing wireless control and programming of the infusion pump. The system may further be adapted to receive analyte data from a continuous blood glucose monitor (a CGM). The data received from the CGM may be stored in the BGM device for later retrieval just as it may be used for open or closed loop control of the infusion pump using appropriate software for calculating infusion parameters based on BGM and/or CGM values.

In a further aspect the invention provides a method of connecting an apparatus (e.g. as described above) to an external electrical connector, comprising the steps of: (a) providing an apparatus comprising an electrical apparatus connector and a port opening arranged in the vicinity of the electrical connector, (b) providing an external electrical connector adapted for releasable connection to the apparatus connector, whereby in a situation of use an electrical contact can be established between the two connectors, wherein the external electrical connector comprises a portion adapted to block the port opening when the external electrical connector is connected to the apparatus connector, and (c) connecting the two connectors thereby preventing insertion of an object in the port opening when the two connectors are connected to each other. The external electrical connector may be connected to an external power source before or after the two connectors have been connected, thereby charging a rechargeable power source arranged in the apparatus.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

Figure 1:
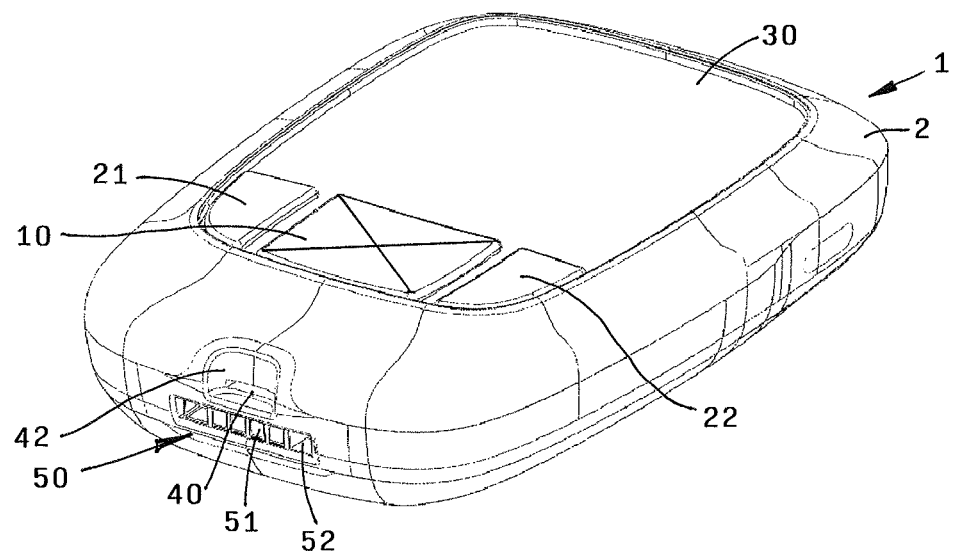
FIG. 1 shows a remote controller with a build-in BGM.

FIG. 1 shows an electronic device in the form of a remote controller (RC) 1 for a drug delivery device (see below) comprising a housing 2 defining an interior, an LCD display 30 arranged at the upper portion of the RC, and user input means in the form of a number of buttons arranged beneath the display. The RC further comprises electronic circuitry arranged in the interior, an electrical housing connector 50 in communication with the exterior, a port opening 40 arranged in a recess 42 in the vicinity of the electrical connector, and an analyte sensor arranged in the housing and in communication with the port opening. The sensor may be a blood glucose sensor adapted to receive a blood glucose test strip, thereby providing the RC with a build-in BGM. Typically, a BGM detects glucose in a blood sample electrochemically, by detecting the oxidation of blood glucose using an enzyme such as glucose oxidase provided as part of a disposable, single-use electrode system, typically in the form of a strip. Examples of devices of this type are disclosed in U.S. Pat. Nos. 5,141,868, 5,286,362, 5,288,636, and 5,437,999 which are incorporated herein by reference.

An external electrical connector (see FIG. 2) is adapted for releasable connection to the housing connector, whereby in a situation of use an electrical contact can be established between the two connectors. The buttons are in the form of a rocker switch 10 and a left ACCEPT key 21 as well as a right ESCAPE key 22. In the shown embodiment the rocker switch serves as navigation key and is a four-way switch having four areas supporting respectively the directions: UP-DOWN and LEFT-RIGHT. Indeed, the four areas of the rocker switch may be replaced with a number of keys arranged in any desired configuration. A more detailed description of a user interface for the shown RC can be found in WO 2007/000427.

Figure 2:
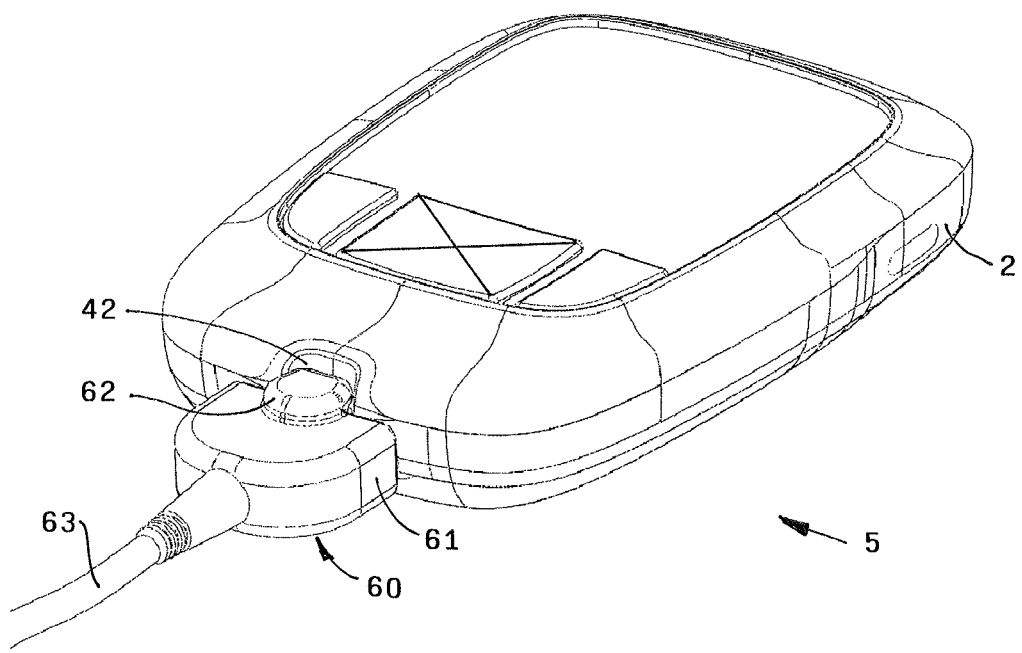
FIG. 2 shows the remote controller of fig. with an electrical connector attached.

FIG. 2 shows an assembly 5 comprising the RC of FIG. 2 with an external electrical connector 60 connected to the electrical housing connector 50. The external electrical connector comprises a main portion 61 connected to a cable 63, and an extending portion 62 adapted to block the port opening when the external electrical connector is connected to the housing connector, thereby preventing insertion of an object in the port opening when the two connectors are connected to each other. In the shown embodiment the connector is adapted for data communication as well as for general power supply to the circuitry and for charging an internal battery. For example, a standard 4-contact USB connector would enable charging from a wall plug or a PC USB port, as well as communication via a PC USB port. More specifically, the RC is provided with a housing connecter 50 comprising 4 electrical contact plates 51 and two female mechanical connectors 52, the housing connector being adapted to engage 4 corresponding electrical contacts and to receive corresponding male connector members. Preferably the mechanical connectors are provided with a snap lock feature securing that the external electrical connector is properly held in place. To secure proper electrical contact the contacts may be spring-biased. Preferably the contacts in the external electrical connector are spring-biased, this allowing the non-moveable housing contacts 51 to be properly sealed against moisture, and to have a generally planar, easy to wipe-off design.

The portion on the external electrical connector adapted to block the port opening when the external connector is connected to the housing connector is a male extension 62 on the connector adapted to engage the recessed portion 41 around the port opening 40, thereby blocking access to the port opening. As the male extension is adapted to positively engage a corresponding female structure, this can be used to prevent incorrect connection of the connector (e.g. trying to connect the connector 180° upside-down) as the housing does not allow the male extension to be fully inserted when not in the correct position.

Figure 3:
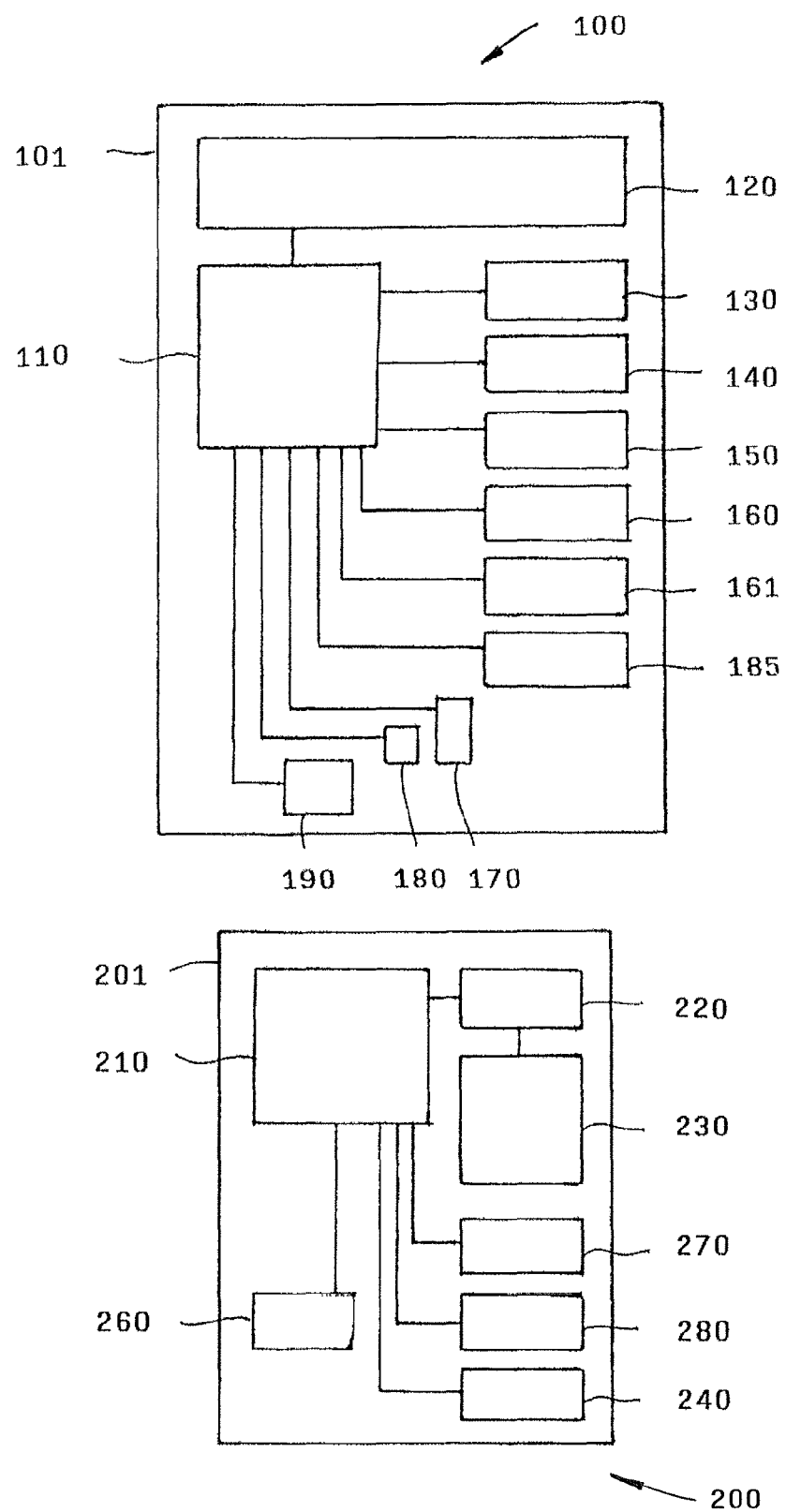
FIG. 3 shows a schematic representation of a remote controller and an infusion pump.

FIG. 3 shows a schematic representation of a medical system comprising a drug delivery device (or pump unit) 200 and a corresponding RC 100. It is considered that the general design of such units is well known to the skilled person, however, for a more detailed description of the circuitry necessary to provide the desired functionality of the present invention reference is made to US 2003/0065308 which is hereby incorporated by reference.

More specifically, FIG. 3 depicts a simplified block diagram of various functional components or modules (i.e. single components or groups of components) included in the pump unit 200 and RC 100. The RC includes a housing 101, a remote processor 110 including a CPU, memory elements for storing control programs and operation data and a clock, a display (e.g. LCD or OLED) 120 for providing information to the user, a keypad 130 for taking input from the user, an audio alarm 140 for providing information to the user, a vibrator 150 for providing information to the user, a main rechargeable battery 160 for supplying power to the controller, a backup battery 161 to provide memory maintenance for the controller, a remote radio frequency (RF) telemetry transmitter 170 for sending signals to the pump unit, a remote radio frequency (RF) telemetry receiver 180 for receiving signals from the pump unit, and a BG sensor module 190. The controller further comprises a combined charging and data exchange port 195 (e.g. of the type described above) as well as a further wireless port 185, e.g. an infrared (IR) or RF input/output system for communicating with a further device, e.g. a BGM, a CGM, a PC or a PDA.

As also depicted in FIG. 3, the pump unit 200 includes a housing 201, pump processor electronics 210 including a CPU and memory elements for storing control programs and operation data, battery 260 for providing power to the system, a pump unit RF telemetry transmitter 270 for sending communication signals to the RC, a pump unit radio frequency (RF) telemetry receiver 280 for receiving signals from the RC, a second pump unit receiver 240, a reservoir 230 for storing a drug, and a pump assembly 220 for expelling drug from the reservoir through a transcutaneous device to the body of a patient. In alternative embodiments the pump unit may also comprise a display (e.g. LCD or OLED) for providing information to the user, a keypad for taking input from the user, and a vibrator or other tactile actuator for providing information to the user. RF transmission may be in accordance with a standard protocol such as Bluetooth®. The pump unit may be of any suitable type, e.g. as disclosed in U.S. Pat. Nos. 6,873,268, 6,936,029, 7,303,549 and WO 2006/077263 which are hereby incorporated by reference.

Figure 4A:
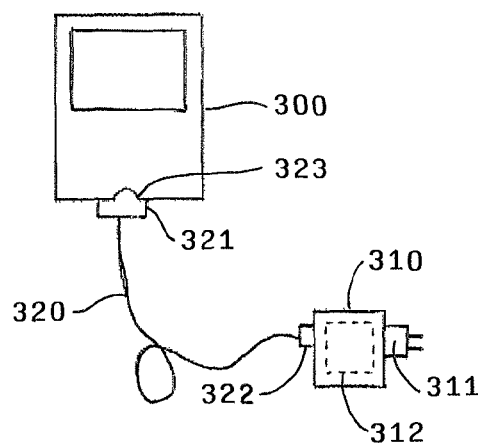
FIGS. 4A-4C show a remote controller with different chargers attached.
Figure 4B:
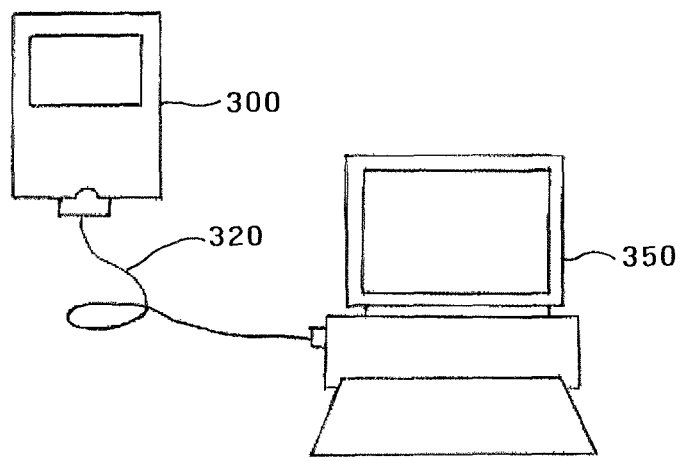
Figure 4C:
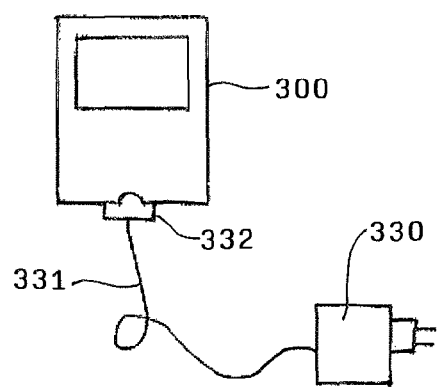

FIGS. 4A-4C shows a RC of the type described with reference to FIGS. 1-3 and connected to different types of power supplies. FIG. 4A shows a RC 300 and power supply unit ("charger" or "power adaptor") 310 comprising a power source connector in the form of a utility power plug 311, e.g. a 100-240V wall plug for a given national standard or a 12-24V plug for a car, as well as a power outlet. Alternatively, the charger may be part of a system comprising a number of exchangeable plugs either connected directly to the charger or via a cable.

The charger comprises electric power circuitry 312 connected to the power source connector and the electric power outlet and adapted to change the inlet voltage of e.g. 100-240V to an outlet voltage of e.g. 5V. The circuitry may be in the form of a traditional step-down transformer or it may be of the electronically controlled type which may then automatically adapt to a given supplied voltage.

The charger is connected to the RC via a USB type cable 320 comprising an electrical device connector 321 of the type described with reference to FIG. 2, and connected to the charger outlet by a charger connector 322. The charger connector is preferably a standard USB connector. The device connector may be a special connector adapted specifically for the RC yet allowing USB connectivity, or it may be a standard type USB connector provided with a port-engaging extension 323. By providing a USB charger connector 322 it is possible to connect the charger cable 320 to a peripheral device with a USB port, e.g. a PDA or a PC 350 as shown in FIG. 4B. In this way the data transfer capability of the USB cable can be used to transfer data to and/or from the RC and the PDA or PC. Depending on the type of peripheral device the USB cable may also be used to re-charge the RC, e.g. when connected to a PC.

FIG. 4C shows the RC 300 connected to a dedicated charger 330 comprising a fixedly attached cable 331 with a connector 332. The housing connector 50 (see FIG. 1) may be of the USB type with the charger connector 332 adapted to engage the power supply contacts, or the two connectors may simply be for electrical charging only with no data transmission capability.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An electronic device assembly, comprising:
   a housing having an interior,
   electric circuitry arranged in the interior,
   an electrical housing connector in communication with the exterior,
   a port opening arranged in the vicinity of the electrical connector,
   an analyte sensor arranged in the housing and in communication with the port opening, and
   an external electrical connector adapted for releasable connection to the housing connector, whereby in a situation of use an electrical contact can be established between the two connectors,
   wherein the external electrical connector comprises a portion adapted to block the port opening when the external electrical connector is connected to the housing connector, thereby preventing insertion of an object in the port opening when the two connectors are connected to each other.

2. An electronic device assembly as in claim 1, further comprising a rechargeable power source electrically connected to the housing connector.

3. An electronic device assembly as in claim 1, further comprising:
a charging apparatus comprising:
an electric power source connector,
an electric outlet in communication with the external electrical connector,
electric power circuitry connected to the power source connector and the electric outlet and adapted to change a characteristic of electric power supplied to the electric circuitry before being supplied the electric outlet.

4. An electronic device assembly as in claim 3, wherein the power circuitry is adapted to change the voltage.

5. An electronic device assembly as in claim 4, wherein the electric power source connector is a utility power plug.

6. An electronic device assembly as in claim 4, wherein the external electrical connector is connected to the electric outlet via a cable.

7. An electronic device assembly as in claim 1, wherein the sensor is a physiological analyte sensor.

8. An electronic device assembly as in claim 7, wherein the sensor is a glucose sensor adapted to receive a blood glucose test strip.

9. An electronic device assembly as in claim 1, wherein the port opening and the analyte sensor are adapted to receive a strip-formed member carrying a specimen to be analyzed by the sensor.

10. An electronic device assembly as in claim 1, wherein the portion adapted to block the port opening prevents incorrect connection of the two connectors.

11. An electronic device assembly as in claim 1, wherein the housing comprises one or more of the features from the group consisting of:
a display for displaying an analyte value, keys allowing a user to enter data and/or commands, a communication port for transmitting and/or receiving data, a wireless receiver for receiving data, a wireless transmitter for transmitting analyte data, and a processor for calculating patient treatment suggestions based on analyte sensor data.

12. A method of connecting an apparatus to an external electrical connector, comprising the steps of:
a) providing an apparatus comprising:
an electrical apparatus connector, and
a port opening arranged in the vicinity of the electrical connector,
b) providing an external electrical connector adapted for releasable connection to the apparatus connector, whereby in a situation of use an electrical contact can be established between the two connectors, wherein the external electrical connector comprises a portion adapted to block the port opening when the external electrical connector is connected to the apparatus connector,
c) connecting the two connectors thereby preventing insertion of an object in the port opening when the two connectors are connected to each other; and
d) before or after the two connectors have been connected, connecting the external electrical connector to an external power source to thereby charge a rechargeable power source arranged in the apparatus.

* * * * *